(12) United States Patent
Sakai et al.

(10) Patent No.: US 7,806,823 B2
(45) Date of Patent: *Oct. 5, 2010

(54) ULTRASONIC DIAGNOSTIC APPARATUS

(75) Inventors: Ryoichi Sakai, Mitaka (JP); Akimitsu Harada, Mitaka (JP); Kozo Nakamura, 2-23-13, Kita-machi, Nerima-ku, Tokyo (JP) 179-0081; Isao Ohnishi, 3-18-22, Asagayakita, Suginami-ku, Tokyo (JP) 166-0001; Jyuntaro Matsuyama, Tokyo (JP); Toshiro Uehara, Tokyo (JP)

(73) Assignees: Aloka Co., Ltd., Tokyo (JP); Kozo Nakamura, Tokyo (JP); Isao Ohnishi, Tokyo (JP)

( * ) Notice: Subject to any disclaimer, the term of this patent is extended or adjusted under 35 U.S.C. 154(b) by 506 days.

This patent is subject to a terminal disclaimer.

(21) Appl. No.: 10/951,322

(22) Filed: Sep. 27, 2004

(65) Prior Publication Data

US 2006/0074311 A1    Apr. 6, 2006

(51) Int. Cl.
   *A61F 5/00*    (2006.01)
(52) U.S. Cl. .................. 600/438; 600/437; 600/441; 600/443; 382/128
(58) Field of Classification Search ............... 600/437, 600/438, 441, 443; 382/128
   See application file for complete search history.

(56) References Cited

U.S. PATENT DOCUMENTS

| | | | |
|---|---|---|---|
| 5,368,044 A | 11/1994 | Cain et al. | |
| 5,474,070 A | 12/1995 | Ophir et al. | |
| 5,524,636 A * | 6/1996 | Sarvazyan et al. | 600/587 |
| 5,678,565 A | 10/1997 | Sarvazyan | |
| 6,132,376 A * | 10/2000 | Hossack et al. | 600/443 |
| 6,270,459 B1 * | 8/2001 | Konofagou et al. | 600/449 |
| 6,520,913 B1 * | 2/2003 | Pesavento et al. | 600/438 |
| 7,107,159 B2 * | 9/2006 | German | 702/41 |
| 2002/0056312 A1 * | 5/2002 | Tamura et al. | 73/61.71 |
| 2002/0103432 A1 * | 8/2002 | Kawchuk | 600/437 |
| 2002/0157478 A1 * | 10/2002 | Seale | 73/789 |
| 2004/0234113 A1 * | 11/2004 | Miga | 382/128 |
| 2006/0120582 A1 * | 6/2006 | Squilla et al. | 382/128 |
| 2006/0184020 A1 * | 8/2006 | Sumi | 600/437 |

FOREIGN PATENT DOCUMENTS

| | | |
|---|---|---|
| EP | 0 737 441 A1 | 10/1996 |
| JP | 9-84788 | 3/1997 |
| JP | 2001-309918 | 11/2001 |

\* cited by examiner

*Primary Examiner*—Long V Le
*Assistant Examiner*—Ellsworth Weatherby
(74) *Attorney, Agent, or Firm*—William L. Androlia; H. Henry Koda (57) ABSTRACT

An echo tracking processor unit detects a bone surface section based on an echo signal and tracks a position of the bone surface section. An interpolation line generator unit generates an interpolation line connecting tracking points which represent the tracked bone surface section. A translational displacement corrector unit removes a translational displacement component between an interpolation line corresponding to a time phase of a no-load state stored in a memory and an interpolation line corresponding to a time phase in a loaded state output from the interpolation line generator unit. A strain calculator unit calculates an amount of strain of bone for each time phase and outputs to a characteristic curve generator unit. The characteristic curve generator unit generates a characteristic curve related to the strain of bone based on a load value output from a load measurement device and the amount of strain of bone output from the strain calculator unit.

12 Claims, 8 Drawing Sheets

ULTRASONIC DIAGNOSTIC APPARATUS

CROSS-REFERENCE TO RELATED APPLICATION

The entire disclosure of Japanese Patent Application No. 2003-91097 including specification, claims, drawings and abstract is incorporated herein by reference in its entirety.

BACKGROUND OF THE INVENTION

1. Field of the Invention

The present invention relates to an ultrasonic diagnostic apparatus and in particular to an ultrasonic diagnostic apparatus for evaluating mechanical characteristics of bone.

2. Description of the Related Art

Easy and quantitative measurements of bone strength are desired for diagnosing bone metabolic diseases such as osteoporosis, judging fracture risk, and quantitatively diagnosing bone union after treatment of bone fracture.

The evaluation of bone formation and bone union depends largely on an X-ray photograph, but it is difficult to quantitatively diagnose the bone strength with an X-ray photograph. As a method of measuring bone strength, conventionally, there is known a strength test of a sample bone of a measurement target. However, in this method, it is necessary to apply an extraction operation of a sample bone, and thus, the method is invasive. As a method of measuring an amount of bone and a bone density, the use of devices such as X-ray CT and DXA (dual-energy x-ray absorptiometry) has been put in practice. However, these devices only measure the amount of bone and cannot provide an evaluation of the bone strength. Moreover, as X-rays are irradiated in these methods, these methods cannot be considered as non-invasive.

Other attempts to quantitatively evaluate the bone strength include a strain gauge method in which a strain gauge is mounted on an external fixator and the strain of the external fixator is measured, a vibration wave method in which a vibration is applied to a bone from the outside and a characteristic frequency is evaluated, and an acoustic emission method in which acoustic waves generated by a bone which has reached the yield stress are detected. These methods, however, have various problems in that there is a limitation to the treatment to which these methods can be applied, that invasion must be applied to the bone, and that the precision is insufficient.

Attempts have been made to analyze fine structures of the bone using ultrasound, but the relationship between the result of this analysis and the bone strength is not yet known (refer to, for example, Japanese Patent Laid-Open Publication No. Hei 9-84788).

SUMMARY OF THE INVENTION

There has been no device in the related art to non-invasively and quantitatively evaluate mechanical characteristics of bone such as bone strength. An advantage of the present invention is that an ultrasonic diagnostic apparatus for non-invasively and quantitatively evaluating mechanical characteristics of bone within a living body is provided.

According to one aspect of the present invention, there is provided an ultrasonic diagnostic apparatus comprising a transceiver unit which generates a plurality of ultrasonic beams with respect to a bone in a subject and obtains a plurality of echo signals corresponding to the ultrasonic beams; and a shape measurement unit which identifies a surface point corresponding to a bone surface for each of the echo signals and generates shape data of the bone surface based on the plurality of surface points obtained from the plurality of echo signals. According to another aspect of the present invention, it is preferable that the ultrasonic diagnostic apparatus further comprises a characteristic evaluation unit which evaluates a mechanical characteristic of the bone based on a change in the shape data when an external action is applied to the bone.

With such a structure, it is possible to non-invasively and quantitatively evaluate mechanical characteristics of the bone within a living body from shape data of a bone surface based on the echo signals.

According to another aspect of the present invention, it is preferable that, in the ultrasonic diagnostic apparatus, the transceiver unit generates the ultrasonic beams within a same cross section of the bone in the subject. According to another aspect of the present invention, it is preferable that, in the ultrasonic diagnostic apparatus, the shape measurement unit comprises a tracking unit which tracks the surface points from a state in which the external action is not applied to a state in which the external action is applied. According to another aspect of the present invention, it is preferable that, in the ultrasonic diagnostic apparatus, the shape measurement unit comprises a shape data generator unit which generates the shape data for each time phase from the state in which the external action is not applied and the state in which the external action is applied.

With such a structure, the transceiver unit generates ultrasonic beams within the same cross section with respect to a bone in the subject and the bone surface points are tracked. Because of this, a bone surface is always detected within the same cross section during the entire measurement period. Therefore, it is possible to obtain very precise shape data. According to another aspect of the present invention, it is preferable that, in the ultrasonic diagnostic apparatus, the shape data generator unit generates, as the shape data, an interpolation line connecting the plurality of surface points for each time phase. With such a structure, it is possible to evaluate a bone on an arbitrary point on the generated interpolation line.

According to another aspect of the present invention, it is preferable that, in the ultrasonic diagnostic apparatus, the characteristic evaluation unit overlaps the interpolation line corresponding to the state in which the external action is not applied and the interpolation line corresponding to the state in which the external action is applied by overlapping one of the interpolation lines on the other to correct a displacement due to a movement of the bone between the two interpolation lines and evaluates the mechanical characteristic of the bone based on the two corrected interpolation lines. With such a structure, even when the bone moves with respect to the transceiver unit during measurement, it is possible to evaluate while correcting the displacement due to the movement of the bone.

According to another aspect of the present invention, there is provided an ultrasonic diagnostic apparatus comprising a transceiver unit which generates a plurality of ultrasonic beams with respect to a bone in a subject and obtains a plurality of echo signals corresponding to the ultrasonic beams; and a tracking unit which identifies a surface point corresponding to a bone surface for each of the echo signals and tracks the surface points from a no-load state in which no load is applied to the bone to a loaded state in which a load is applied to the bone.

According to another aspect of the present invention, it is preferable that the ultrasonic diagnostic apparatus further comprises an interpolation line generator unit which generates an interpolation line connecting a plurality of surface points for each time phase in the no-load state and in the loaded state. According to another aspect of the present invention, it is preferable that the ultrasonic diagnostic apparatus further comprises a translational displacement corrector unit which translates one of the interpolation line corresponding to the no-load state and the interpolation line corresponding to the loaded state such that one of the interpolation lines is over the other interpolation line and corrects a translational displacement component between the two interpolation lines.

According to another aspect of the present invention, it is preferable that the ultrasonic diagnostic apparatus further comprises a strain calculator unit which calculates an amount of strain of the bone in the loaded state based on the two interpolation lines in which the translational displacement component is corrected. According to another aspect of the present invention, it is preferable that the ultrasonic diagnostic apparatus further comprises a characteristic curve generator unit which generates a characteristic curve indicating a relationship between the load value and the amount of strain of the bone in the loaded state. According to another aspect of the present invention, it is preferable that the ultrasonic diagnostic apparatus further comprises a display unit which displays a cross sectional image of the bone based on the plurality of echo signal, wherein the display unit displays the interpolation line at a suitable position on the cross sectional image of the bone.

BRIEF DESCRIPTION OF THE DRAWINGS

A preferred embodiment of the present invention will be described in detail based on the following figures, wherein.

DESCRIPTION OF PREFERRED EMBODIMENT

A preferred embodiment of the present invention will now be described referring to the drawings.

Figure 1:
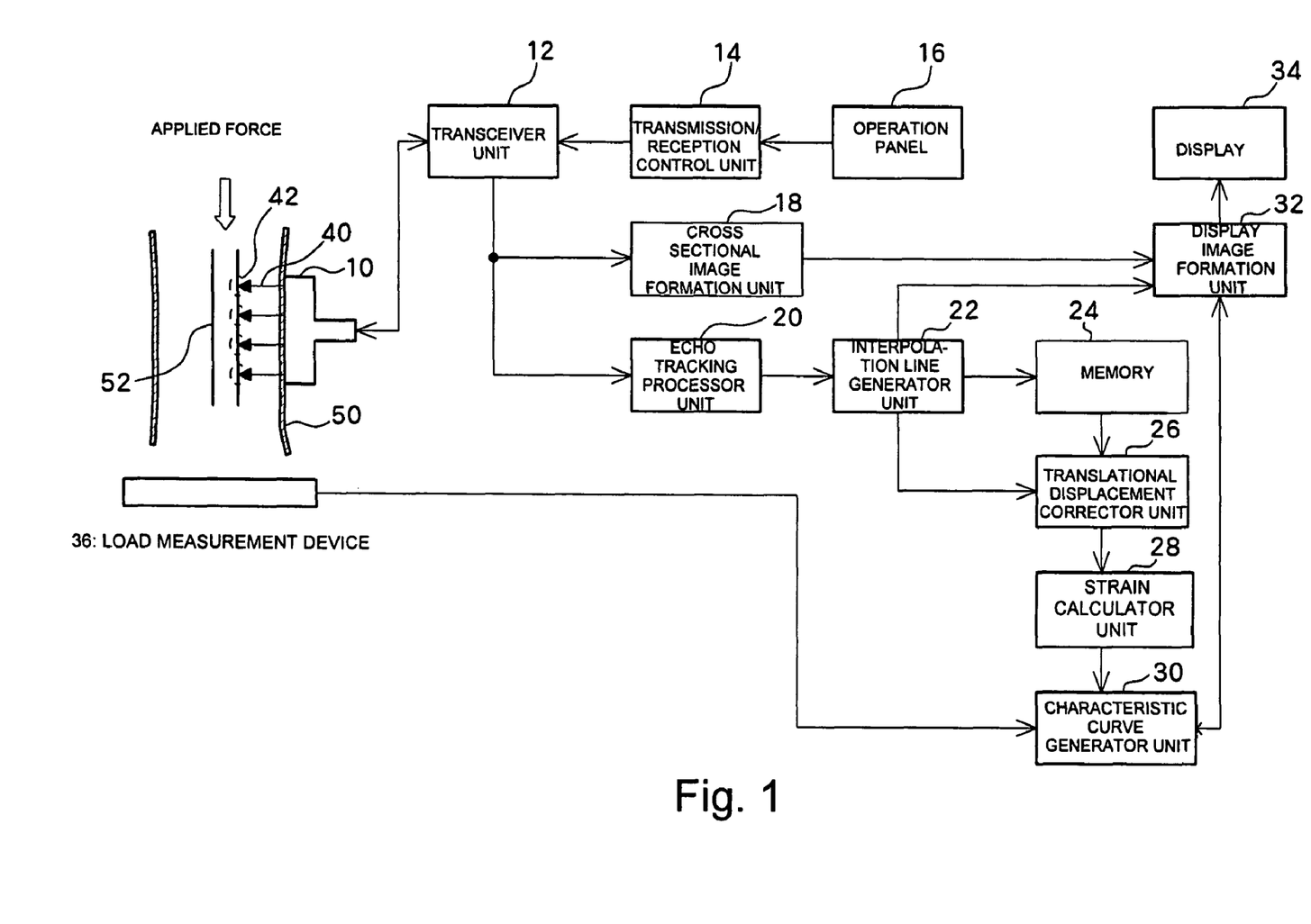
FIG. 1 is a block diagram showing an overall structure of an ultrasonic diagnostic apparatus according to a preferred embodiment of the present invention.

FIG. 1 shows a preferred embodiment of an ultrasonic diagnostic apparatus according to the present invention. FIG. 1 is a block diagram showing an overall structure of the ultrasonic diagnostic apparatus. A probe 10 is an ultrasonic probe used in contact with a surface of the body of a subject 50. Alternatively, an ultrasonic probe which is inserted into the subject may be used. The probe 10 transmits and receives ultrasonic beams 40 to and from a bone 52 within the body of the subject 50. Tracking points 42 which are set on the bone 52 will be described later. As the probe 10, it is desirable to use a linear electronic scan probe (linear array probe) which electronically scans the ultrasonic beam 40.

A transceiver unit 12 controls the probe 10 and electronically scans the ultrasonic beam 40 on a cross sectional surface (a cut surface of a subject in FIG. 1). When the probe 10 is a linear probe, for example, sequential electronic scanning of 120 ultrasonic beams 40 (FIG. 1 only shows 4 ultrasonic beams for echo tracking which will be described later) is applied and an echo signal is obtained for each ultrasonic beam 40. The plurality of obtained echo signals are output to a cross sectional image formation unit 18 and the cross sectional image formation unit 18 forms a cross sectional image (B mode image) of the bone based on the plurality of echo signals.

The echo signal obtained in the transceiver unit 12 is also output to an echo tracking processor unit 20. The echo tracking processor unit 20 applies an echo tracking process in which the bone surface section is extracted from each echo signal and is tracked. For the echo tracking process, for example, a technique detailed in Japanese Patent Laid-Open Publication No. 2001-309918 is used. For the echo tracking process, for example, 4 tracking echo signals are used. The tracking echo signals may be selected from among the echo signals used for forming a cross sectional image (for example, 120 echo signals) or may alternatively be obtained by interrupting formation of the cross sectional image and obtaining the 4 tracking echo signals.

The 4 ultrasonic beams 40 shown in FIG. 1 correspond to the 4 tracking echo signals. An examiner inputs an instruction related to transmission/reception of the ultrasound through an operation panel 16 to a transmission/reception control unit 14 and the transmission/reception control unit 14 controls the transceiver unit 12 based on the instruction from the examiner. With this structure, ultrasonic beams 40 for obtaining tracking echo signals are transmitted to a diagnosis site on the bone surface according to the instruction from the examiner. In the transmission/reception of ultrasound, a strong reflected wave is obtained from the bone surface. Therefore, the echo signals obtained from within the body of the diagnosis target (subject) are obtained as having large amplitude in a portion corresponding to the bone surface.

Figure 2:
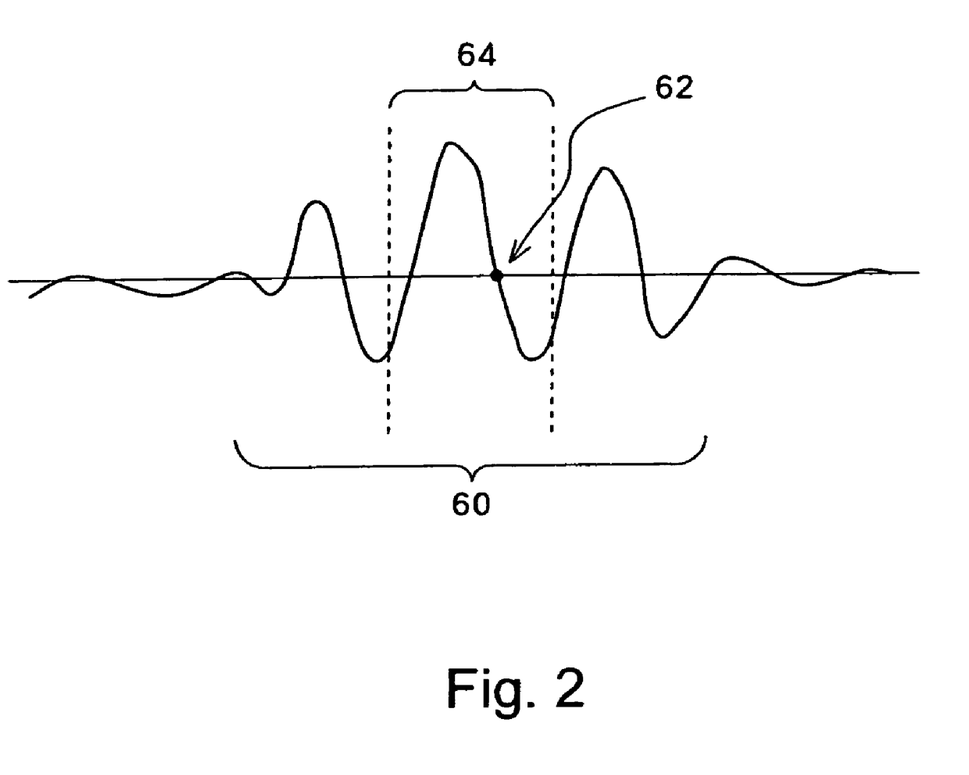
FIG. 2 is a diagram schematically showing each echo signal.

FIG. 2 is a diagram schematically showing a bone surface section of the echo signals. As shown in FIG. 2, each echo signal includes a range 60 in which the echo signal has a large amplitude corresponding to the bone surface. When the bone surface section is considered simply as a portion with a large amplitude, it is unclear as to which portion in the range 60 corresponds to the surface section and, as a result, there is an error of approximately the range 60. In the echo tracking process, a zero-cross point 62 is detected as a representative of each echo signal and the detected zero-cross point 62 is tracked to significantly increase the precision of the bone surface position.

The zero-cross point 62 is detected as a time, within a tracking gate period 64, at which the polarity of the echo signal is inverted from positive to negative or from negative to positive. In FIG. 2, the time at which the polarity of the echo signal is inverted from positive to negative is the zero-cross point 62. When the zero-cross point 62 is detected, a new tracking gate is set with the detected zero-cross point 62 as its center. In the echo signal obtained at the next time, a zero-cross point 62 is detected within the newly set tracking gate period 64. In this manner, a zero-cross point 62 is tracked as the bone surface point for each echo signal.

Figure 3:
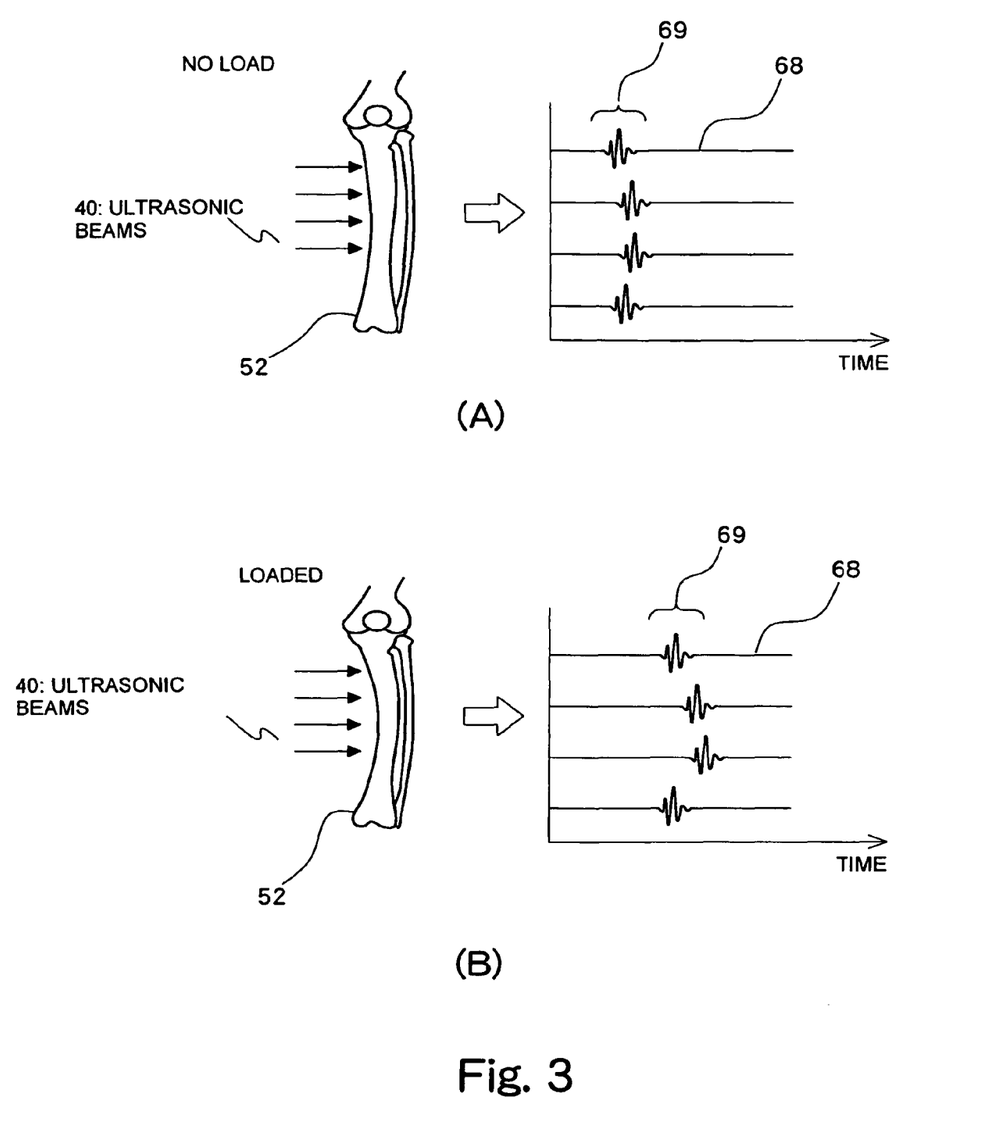
FIG. 3 is a diagram for explaining tracking of a bone surface section by the echo signals.

FIG. 3 is a diagram for explaining tracking of a bone surface section by 4 echo signals. In an evaluation of the mechanical characteristics of bone using the ultrasonic diagnostic apparatus of the present invention, a shape of the bone is compared between a state in which no load is applied to the bone (no-load state) and a state in which a load is applied (loaded state). FIG. 3 shows tracking in each of the no-load state and the loaded state.

FIG. 3 (A) shows tracking with respect to the bone 52 in the no-load state. Echo signals 68 corresponding to 4 ultrasonic beams 40 applied toward the bone 52 indicate a large amplitude (an amplitude maximum portion 69) at a section corresponding to the bone surface. It is possible to know the shape of the bone surface based on the position of the amplitude maximum portion 69 in each echo signal 68 (obtained time of the waveform). Because the zero-cross point (reference numeral 62 in FIG. 2) is detected as a surface point within the amplitude maximum portion 69, the position of the bone surface is very precisely identified.

FIG. 3 (B) shows tracking with respect to the bone 52 in the loaded state. Similar to FIG. 3 (A), the shape of the bone surface can be known based on the echo signals 68 corresponding to the 4 ultrasonic beams 40. Because a load is applied, strain (bending of bone) of the bone 52 in FIG. 3 (B) is larger than that in FIG. 3 (A). Although an example configuration with 4 tracking echo signals is shown in FIG. 3, it is also possible to measure with a plurality of tracking echo signals, the number being different from 4.

Referring again to FIG. 1, a surface point which is tracked for each echo signal, that is, for each ultrasonic beam 40 in the echo tracking processor unit 20 is the tracking point 42. An interpolation line generator unit 22 generates an interpolation line connecting these tracking points 42. That is, by interpolating with a curve among a plurality of tracking points 42 using a spline interpolation or a least square interpolation, an interpolation line is calculated. By increasing the number of echo signals for echo tracking process it is possible to more precisely approximate the surface shape of the bone by the interpolation line.

When a mechanically specific section exists in a bone, an interpolation line is calculated considering the specific section. For example, when there is a fracture in the bone, it is possible to form interpolation lines for the portions of the bone separated by the bone fracture and to combine these two interpolation lines to form an interpolation line for the bone as a whole. The interpolation line is calculated for each time phase and is output to a memory 24, a translational displacement corrector unit 26, and a display image formation unit 32. The translational displacement corrector unit 26 cancels a translational displacement component between an interpolation line corresponding to a time phase in the no-load state stored in the memory 24 and an interpolation line corresponding to a time phase in the loaded state output from the interpolation line generator unit 22.

Figure 4:
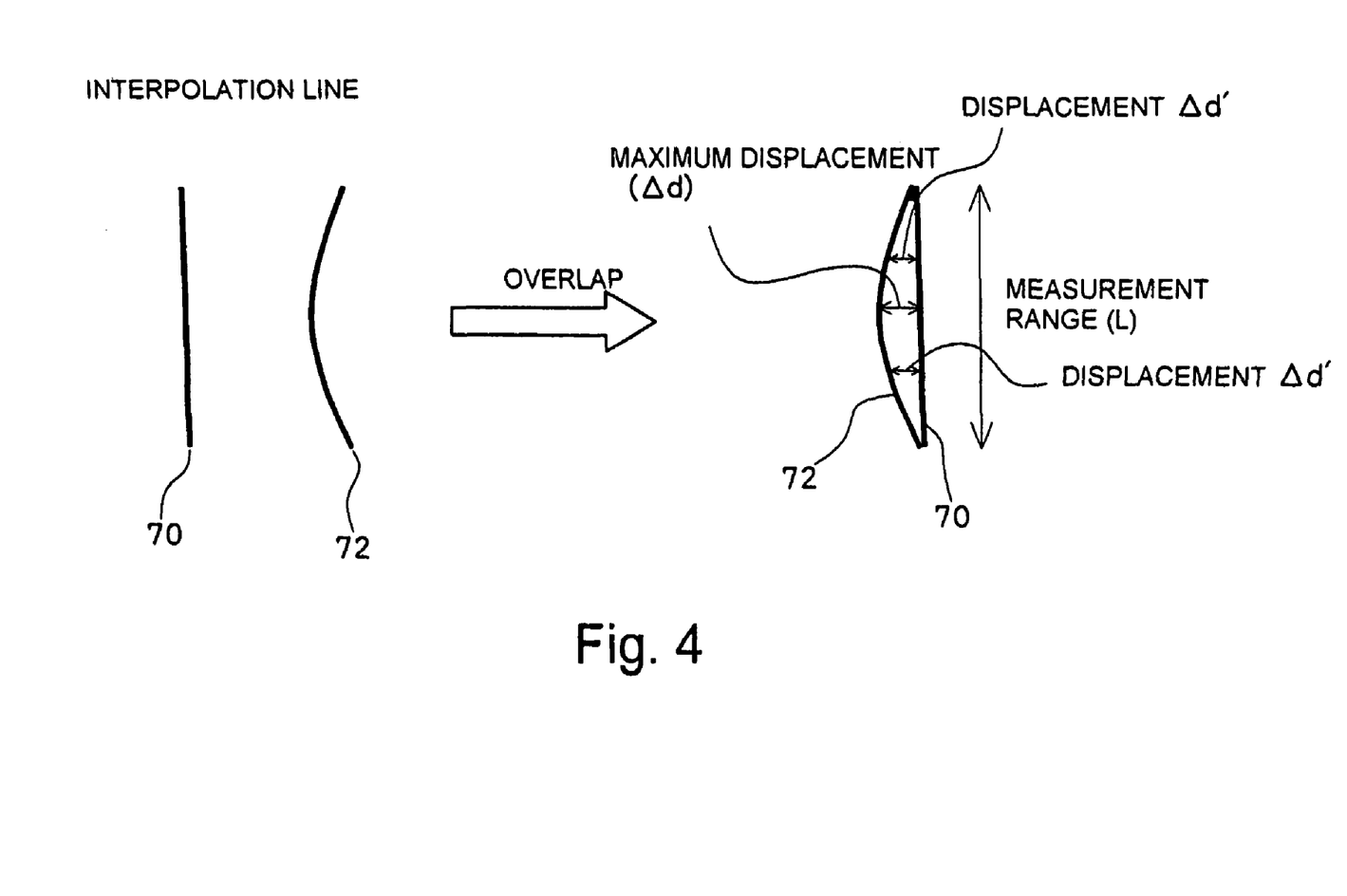
FIG. 4 is a diagram for explaining the operation to cancel a translational displacement component.

FIG. 4 is a diagram for explaining a cancel operation of the translational displacement component in the translational displacement corrector unit 26. The translational displacement corrector unit 26 overlaps the interpolation line corresponding to the no-load state (no-load-state interpolation line 70) and the interpolation line corresponding to the loaded state (loaded-state interpolation line 72) on each other to cancel the translational displacement component. The overlapping of the interpolation lines is performed, for example, by matching the ends of the no-load-state interpolation line 70 and the loaded-state interpolation line 72. By performing the overlapping operation, it is possible to cancel out the translational displacement between interpolation lines due to a movement of the bone during measurement. With this structure, an amount of strain of the bone is very precisely extracted from a difference between the no-load-state interpolation line 70 and the loaded-state interpolation line 72 which are overlapped. An amount $\epsilon$ of strain of the bone is defined, based on a maximum displacement $\Delta d$ between the overlapped no-load-state interpolation line 70 and loaded-state interpolation line 72 and a measurement range (length of the no-load-state interpolation line 70) L, as $\epsilon=\Delta d/L$. When a displacement at an arbitrary point between the no-load-state interpolation line 70 and the loaded-state interpolation line 72 is $\Delta d'$, it is possible to calculate $\epsilon'=\Delta d'/L$ as the amount of strain of the bone.

Referring again to FIG. 1, a strain calculator unit 28 calculates an amount $\epsilon$ of strain of the bone and outputs to a characteristic curve generator unit 30. The characteristic curve generator unit 30 generates a characteristic curve regarding the strain of the bone based on a load value output by a load measurement device 36 and an amount of strain of bone output by the strain calculator unit 28.

Figure 5:
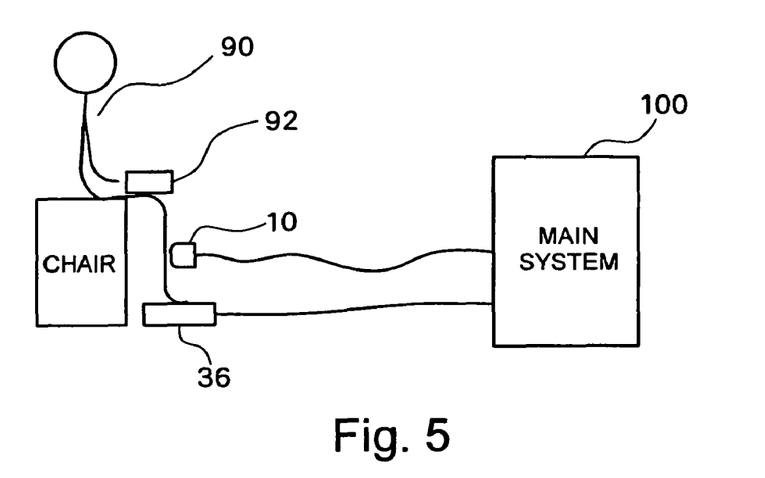
FIG. 5 is a diagram showing a method of diagnosing the tibia using an ultrasonic diagnostic apparatus according to a preferred embodiment of the present invention.

A method for diagnosing mechanical characteristics of a bone using the ultrasonic diagnostic apparatus according to the preferred embodiment of the present invention will now be described. FIG. 5 is a diagram showing a method for diagnosing the tibia using the ultrasonic diagnostic apparatus of FIG. 1. A weight 92 is placed on the lap of a subject 90 who is sitting on a chair so that a load due to the weight 92 is applied to the tibia. The load value due to the weight 92 is measured by the load measurement device 36 and is output to a main system 100 of the ultrasonic diagnosis device. The probe 10 is fixed by a probe fixer which is not shown and transmits and receives ultrasound to and from the crus (a site of the tibia).

Figure 6:
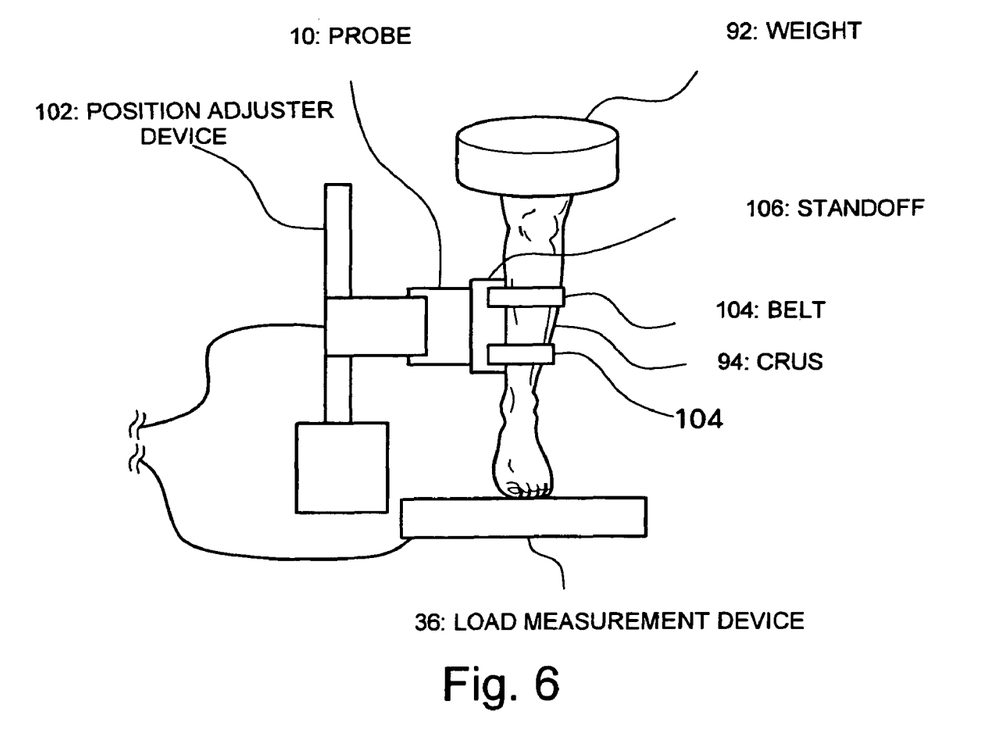
FIG. 6 is a diagram showing a method of fixing a probe.

A positional relationship among the probe 10, crus, and probe fixer is shown in FIG. 6. The probe 10 is supported by a position adjuster device 102 which functions as a probe fixer and placed in a predetermined position. A load due to the weight 92 is applied to the crus 94 of the subject and the load value is measured by the load measurement device 36. A standoff 106 is mounted on the crus 94 with a belt 104. The standoff 106 is a gel-like medium which allows ultrasound to transmit through and has an acoustic impedance which is close to that of a living body. The probe 10 is placed in contact with the standoff 106 and transmits and receives ultrasound to and from the crus 94 of the subject via the standoff 106, to evaluate the mechanical characteristics of the tibia or fibula.

Figure 7:
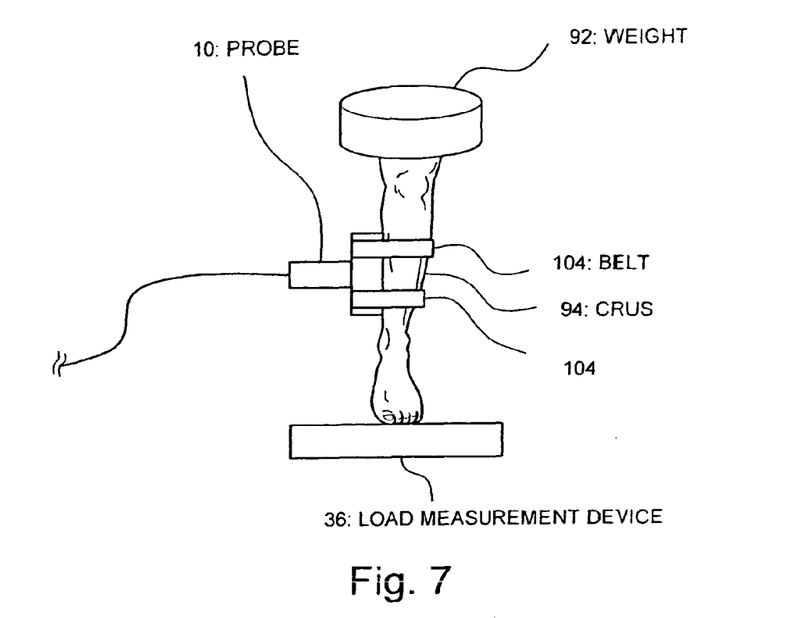
FIG. 7 is a diagram showing another method of fixing a probe.
Figure 8:
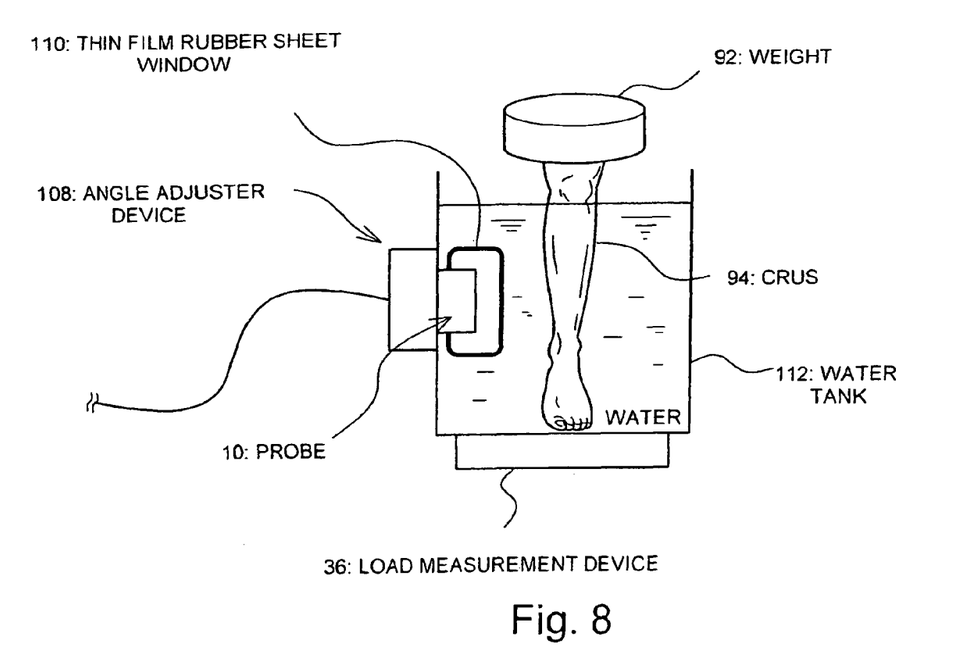
FIG. 8 is a diagram showing another method of fixing a probe.

FIGS. 7 and 8 show other examples of methods for fixing the probe 10. In the example configuration of FIG. 7, the probe 10 is placed in contact with the crus 94 using the belt 104. In the example configuration of FIG. 8, the subject places the crus 94 in a water tank 112 and the probe 10 is fixed by an angle adjuster device 108 mounted on the water tank 112. The probe 10 is covered by a thin film rubber sheet window 110 and transmits and receives ultrasound to and from the crus 94 via water. In a practical setting, it is desirable that a fixing device which is not shown is provided so that the position of the crus 94 with respect to the probe 10 does not change. In the example configurations of FIGS. 7 and 8 also, the load value due to the weight 92 is measured by a load measurement device 36.

Figure 9:
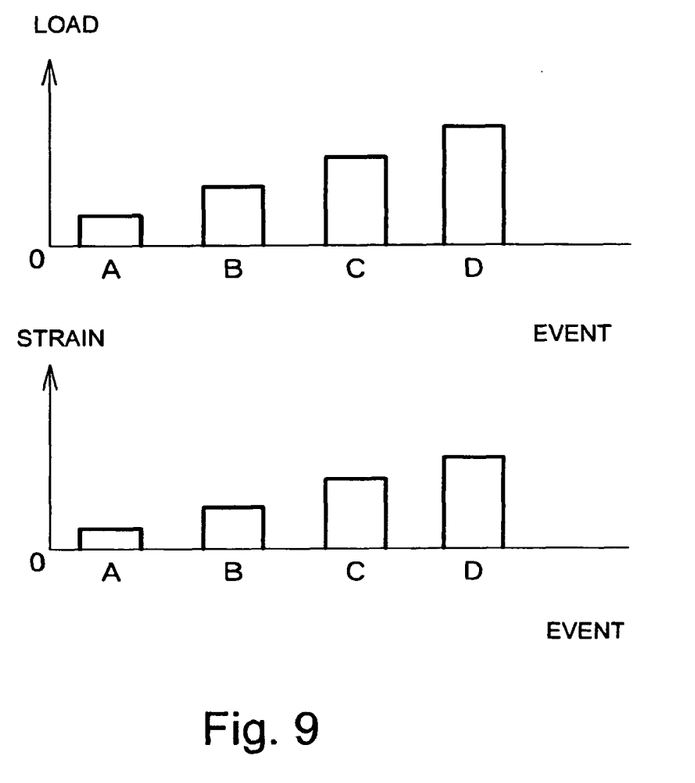
FIG. 9 is a diagram showing an example of a characteristic curve of a change with respect to time of load and strain, generated by a characteristic curve generator unit.
Figure 10:
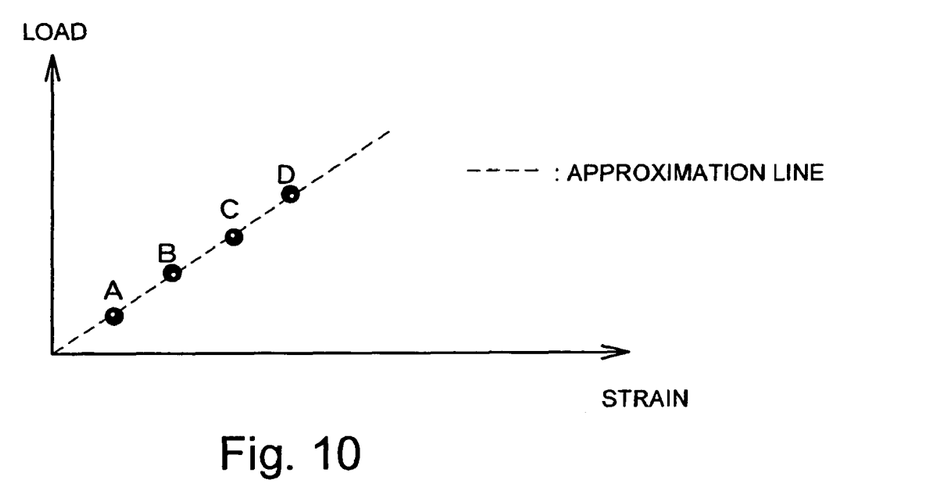
FIG. 10 is a diagram showing an example of a characteristic curve showing a relationship between a load and strain, generated by a characteristic curve generator unit.

By changing the weight 92, it is possible to measure strain for each load value. Based on data obtained through this process, the characteristic curve generator unit 30 generates a characteristic curve. FIGS. 9 and 10 show examples of characteristic curves generated by the characteristic curve generator unit 30. FIG. 9 is a diagram showing each of a load value and an amount of strain of bone with the horizontal axis taken as an event (four stages of A, B, C, and D). It can be seen that, when the load value is increased stepwise in the order of events A, B, C, and D, the amount of strain of bone correspondingly increases in a stepwise manner.

FIG. 10 is a diagram showing a relationship between the amount of strain of bone and the load value shown in FIG. 9, with the horizontal axis representing the amount of strain of bone and the vertical axis representing the load value. FIG. 10 also shows an approximation line calculated with data discretely obtained in the four stages of A, B, C, and D. The characteristic curves shown in FIGS. 9 and 10 are displayed on a display (reference numeral 34 of FIG. 1) through a display image formation unit (reference numeral 32 of FIG. 1).

As a mechanical characteristic of bone, for example, it is possible to quantify (load)/(strain) which is a slope of the approximation line in FIG. 10, as a measure of the rigidity of the bone. For example, when an average value for healthy subjects is A and the value for the patient is B, it is determined that the rigidity of the bone of the diagnosis target (subject) is normal when the value of B is within a predetermined range estimated from the value of A and that the rigidity of the bone of the diagnosis target is abnormal when the value of B is outside the range. It is also possible to evaluate the rigidity of the bone from a difference, (B−A).

It is also possible to evaluate a strength of bone by applying a weight load which is an external action to the bone and quantifying plastic deformation of the bone after the weight is removed. As a concrete example, it is possible to compare the position of a surface of the bone before a load is applied and the position of the surface of the bone after a load is applied and then removed. It is possible to determine that the strength of the bone is normal when the difference is within a predetermined range and that the strength of the bone is abnormal when the difference is outside the range.

Other methods for applying a load to the tibia include standing on one foot, standing on both feet, and cycle load by walking. In any of these methods, the load value can be measured by the load measurement device (reference numeral 36 in FIG. 1) similar to the above-described configuration.

Figure 11:
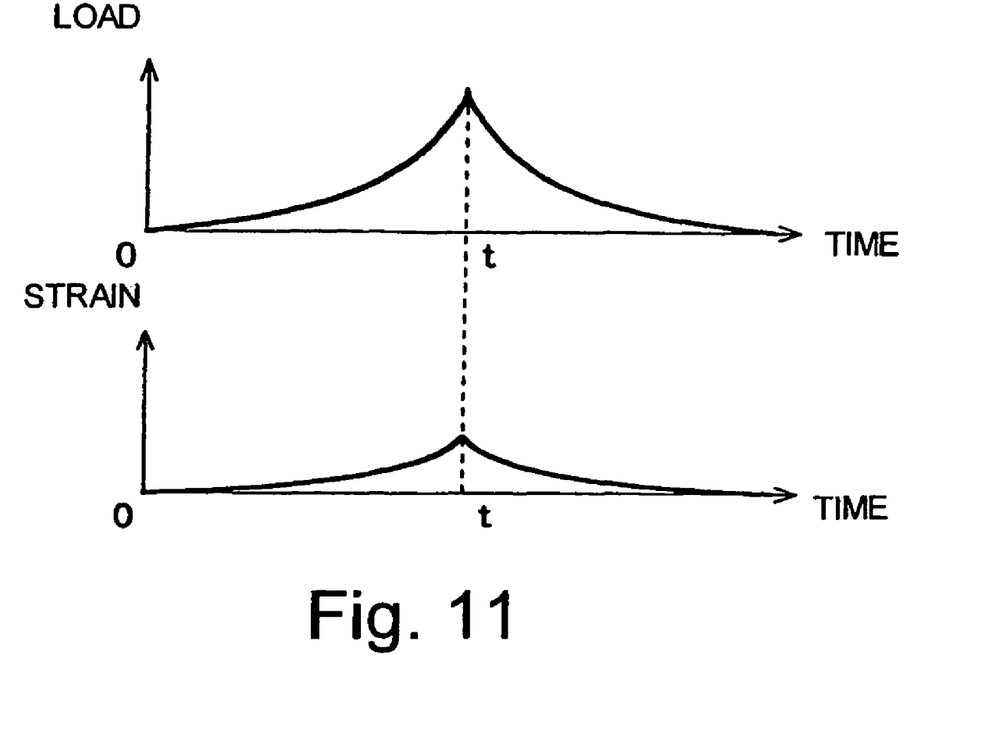
FIG. 11 is a diagram showing another example of a characteristic curve showing a change with respect to time of a load and strain, generated by a characteristic curve generator unit.
Figure 12:
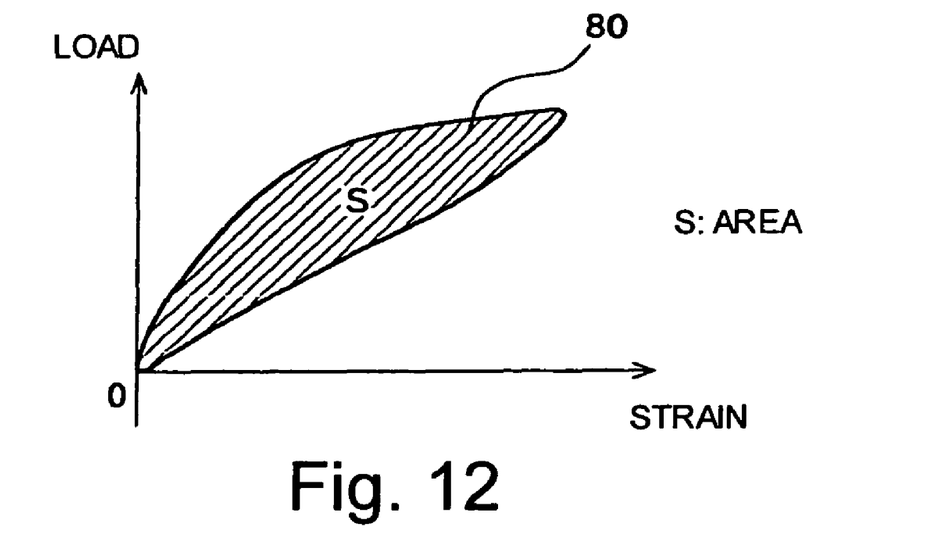
FIG. 12 is a diagram showing a hysteresis characteristic curve of a load and strain, generated by a characteristic curve generator unit.

FIGS. 11 and 12 show examples of characteristic curves generated by the characteristic curve generator unit 30 in the case of a cycle load. FIG. 11 is a characteristic curve showing each of the load value and amount of strain of the bone with the horizontal axis representing time. FIG. 11 shows that when the load value is gradually increased from time 0 to time t, the amount of strain correspondingly gradually increases from time 0 to time t. It can also be seen that when the load value is gradually reduced after time t, the amount of strain is also gradually reduced. The characteristic curve of FIG. 11 is displayed on a display (reference numeral 34 in FIG. 1) through a display image formation unit (reference numeral 32 in FIG. 1). The examiner can read the amount of strain of the bone corresponding to a load value from the characteristic curve displayed on the display 34.

FIG. 12 shows a characteristic curve in which the horizontal axis represents an amount of strain of the bone and the vertical axis represents a load value. There is a hysteresis characteristic between the amount of load to the bone and the amount of strain of the bone. In other words, an increase characteristic of the amount of strain of the bone when the load value is gradually increased to the maximum load value and a decrease characteristic of the amount of strain of the bone when the load is gradually reduced from the maximum load value would not be the same curve. FIG. 12 shows a characteristic when the load value is increased to a maximum load value and then reduced from the maximum load value. The area of a region 80 reflects the hysteresis characteristic between the load value and the amount of strain. The characteristic curve shown in FIG. 12 is displayed on the display (reference numeral 34 of FIG. 1) through the display image formation unit (reference numeral 32 of FIG. 1).

Referring again to FIG. 1, the display image formation unit 32 forms a display image based on the cross sectional image of the bone formed in the cross sectional image formation unit 18 and the characteristic curve generated by the characteristic curve generator unit 30 and displays the formed image on the display 34. The cross sectional image and the characteristic curve are, for example, switched and displayed based on an instruction by the examiner. Alternatively, the cross sectional image and the characteristic curve may be simultaneously displayed. Moreover, it is also possible to display the interpolation line calculated by the interpolation line generator unit 22, overlapped over the cross sectional image of the bone.

The mechanical characteristic thus obtained such as the amount of strain or strength of bone is an important measure of a quantitative evaluation of bone union and significantly contributes as objective and reliable base data of diagnosis in judgment of effects by an agent to an increase in the bone strength, removal of a fixator/implant, and instruction of degree of load to a patient.

The diagnosis target bone of the ultrasonic diagnostic apparatus according to the present invention is not limited to the tibia and the fibula, and may alternatively applied to, for example, femur and arm bones. When the femur is to be targeted, it is possible to place, on a load measurement device, a diagnosis target wrapping around a weight and diagnose with the probe contacting the femur, to measure the load value applied to the femur and the shape of the femur. When the arm bones are targeted, it is possible to contact the probe on the arm of the subject and to diagnose while the arm is loaded by the subject pushing, with the arm, a load measurement device mounted on a wall. Alternatively, it is also possible for the subject to place his arm on the load measurement device placed on the floor and to diagnose the loaded state in a position of "push-up". In this manner, the ultrasonic diagnostic apparatus of the present invention can be applied to the bones of various regions in the subject.

A diagnosis using the ultrasonic diagnostic apparatus of the present invention is advantageous in that the diagnosis can be applied independent of the method of treatment of bone fracture.

As described, with the ultrasonic diagnostic apparatus of the present invention, it is possible to non-invasively and quantitatively evaluate a mechanical characteristic of the bone within a living body.

What is claimed is:

1. An ultrasonic diagnostic apparatus comprising:
a transceiver unit configured to generate a plurality of ultrasonic beams with respect to a bone in a subject and obtains an echo signal for each of the ultrasonic beams;
a tracking unit configured to identify, for each of the ultrasonic beams, a surface point corresponding to a bone surface based on the echo signal corresponding to the ultrasonic beam, and tracks the surface point of the ultrasonic beam;
a shape generator unit configured to generate shape data of the bone surface based on the plurality of surface points corresponding to the plurality of ultrasonic beams; and
a characteristic evaluation unit for evaluating a mechanical characteristic of the bone based on a change in a shape of the bone obtained from the shape data when an external action is applied to the bone, wherein the tracking unit is further configured to track the surface points from a state in which the external action is not applied to a state in which the external action is applied, the shape generator unit is further configured to generate, as the shape data, an interpolation line based on the plurality of surface points in the state in which the external action is not applied and an interpolation line based on the plurality of surface points in the state in which the external action is applied, and the characteristic evaluation unit is further configured to overlap two interpolation lines, one interpolation line corresponding to the state in which the external action is not applied and the other interpolation line corresponding to the state in which the external action is applied by matching both ends of one of the interpolation lines and both ends of the other interpolation line to correct a displacement between the two interpolation lines due to a movement of the bone, and evaluate the mechanical characteristic of the bone based on the two corrected interpolation lines.

2. The ultrasonic diagnostic apparatus according to claim 1, wherein the characteristic evaluation unit is further configured to measure the change in the shape of the bone by comparing a bone shape with no external action applied to the bone and a bone shape with an external action applied to the bone based on the shape data of the bone with and without the external action applied to the bone.

3. The ultrasonic diagnostic apparatus according to claim 2, wherein the transceiver unit is further configured to generate the ultrasonic beams within a same cross section of the bone in the subject.

4. An ultrasonic diagnostic apparatus comprising:

a transceiver unit configured to generate a plurality of ultrasonic beams with respect to a bone in a subject and obtains an echo signal for each of the ultrasonic beams; and a tracking unit configured to identify a surface point corresponding to a bone surface for each of the ultrasonic beams based on the echo signal corresponding to the ultrasonic beam, and tracks the surface points so as to follow a movement of the bone surface for a plurality of time phases; and a shape data generator unit configured to generate, as shape data, an interpolation line connecting the plurality of surface points for each time phase; and a characteristic evaluation unit configured to evaluate a hysteresis characteristic of the bone based on the shape data obtained for each of the time phases; wherein the characteristic evaluation unit is further configured to overlap two interpolation lines, one interpolation line corresponding to a time phase in which no load is applied to the bone and the other interpolation line corresponding to a time phase in which a load is applied to the bone by matching both ends of the two interpolation lines to correct a displacement between the two interpolation lines due to a movement of the bone, and generate a characteristic curve indicating a relationship between a value of the load applied to the bone and an amount of stain of the bone obtained from the shape data by gradually increasing and then gradually decreasing the value of the load.

5. An ultrasonic diagnostic apparatus according to claim 4, wherein the tracking unit is further configured to detect a zero-cross point as the surface point and tracks the detected zero-cross point, and the zero-cross point is detected as a time at which a polarity of the echo signal is inverted from positive to negative or from negative to positive within a tracking gate period.

6. The ultrasonic diagnostic apparatus according to claim 4, wherein the shape data generator unit is further configured to generate an interpolation line using a spline interpolation.

7. An ultrasonic diagnostic apparatus according to claim 4, wherein the shape data generator unit is further configured to generate an interpolation line using a least square interpolation.

8. The ultrasonic diagnostic apparatus according to claim 4, further comprising:

a strain calculator unit configured to calculate an amount of strain of the bone in a loaded state based on the two interpolation lines in which the displacement is corrected.

9. The ultrasonic diagnostic apparatus according to claim 8, wherein the characteristic evaluation unit configured to generate a characteristic curve indicating a relationship between the value of the load and the amount of strain of the bone in the loaded state.

10. The ultrasonic diagnostic apparatus according to claim 9, wherein the characteristic evaluation unit is further configured to generate a characteristic curve in which one axis represents time and another axis represents the load value.

11. The ultrasonic diagnostic apparatus according to claim 9, wherein the characteristic evaluation unit is further configured to generate a characteristic curve in which one axis represents time and another axis represents the amount of strain of the bone.

12. The ultrasonic diagnostic apparatus according to claim 9, further comprising:

a display unit configured to display a cross sectional image of the bone based on the plurality of echo signals, wherein the display unit displays the interpolation line at a suitable position on the cross sectional image of the bone.

* * * * *